United States Patent [19]

Shami

[11] Patent Number: 4,599,314
[45] Date of Patent: Jul. 8, 1986

[54] MULTIPLE VESSEL SPECIMEN TRAY WITH LID FOR RELEASABLY ADHERING VESSEL COVERS

[75] Inventor: Yehezkel Shami, Toronto, Canada

[73] Assignee: HSC Research Development Corporation, Toronto, Canada

[21] Appl. No.: 504,182

[22] Filed: Jun. 14, 1983

[51] Int. Cl.$^4$ .............................................. C12M 1/00
[52] U.S. Cl. .................... 435/287; 206/509; 206/511; 206/558; 206/563; 220/23.4; 220/23.6; 294/160; 294/161; 422/58; 422/102; 435/296; 435/297; 435/298; 435/300; 435/809; 435/819

[58] Field of Search .............. 435/296, 297, 287, 298, 435/300, 310, 317, 808, 809, 810, 819; 422/58, 102; 206/509, 511, 558, 562, 563; 220/23.4, 23.6; 294/159, 160, 161

[56] References Cited

U.S. PATENT DOCUMENTS

| | | | |
|---|---|---|---|
| 938,675 | 11/1909 | Lorenz | 206/563 |
| 3,190,731 | 3/1961 | Weiskopf | 422/102 |
| 3,300,055 | 12/1964 | Rohr | 211/74 |
| 3,483,997 | 7/1967 | Ritter | 211/76 |
| 3,635,350 | 1/1972 | Wolf | 220/23.6 |
| 3,649,464 | 12/1969 | Freeman | 206/562 |
| 4,090,920 | 5/1978 | Studer | 435/808 |
| 4,136,429 | 1/1979 | Brandes | 29/235 |
| 4,154,795 | 5/1979 | Thorne | 220/23.4 |
| 4,160,803 | 7/1979 | Potts | 206/511 |
| 4,349,109 | 9/1982 | Scordato et al. | 206/562 |

FOREIGN PATENT DOCUMENTS 2051581  5/1972  Fed. Rep. of Germany .

*Primary Examiner*—Sam Rosen
*Assistant Examiner*—William J. Herald
*Attorney, Agent, or Firm*—Rogers, Bereskin & Parr

[57] ABSTRACT

A specimen tray apparatus is disclosed primarily for use in cell culture studies. The apparatus includes a tray and a plurality of individual cells in the form of specimen vessels which can be removably located in the tray. A lid is also provided for the tray and is physically identical therewith. Each vessel has a cover which is received in an opening in the lid when the tray and lid are assembled, so that pressure sensitive tape can then be used to releasably secure the covers to the lid while allowing one or more of the covers to be released when appropriate by peeling back the tape.

8 Claims, 3 Drawing Figures

MULTIPLE VESSEL SPECIMEN TRAY WITH LID FOR RELEASABLY ADHERING VESSEL COVERS

This invention relates generally to a specimen tray apparatus, e.g. for use in growing cell cultures or in clinical chemistry.

In the study of cell cultures, it is often desirable to be able to treat several different cell specimens at the same time. While this type of study can of course be conducted using several specimen dishes, each having a single recess or "well" for receiving a specimen, it often more convenient to use a multiple well specimen dish. A conventional multiple well dish may take the form of a one-piece plastic moulding shaped to provide, typically, 24 wells arranged in a 6×4 array (four rows of six wells each). The dish is normally also provided with a cover which includes a flat top plate for simultaneously closing the tops of all of the wells.

So-called "kinetic" studies are conducted by first treating all of the specimens in the same manner followed by time dependent study of individual specimens or groups of specimens. For example, it could be appropriate to take 24 similar cell specimens, treat all of the specimens at the same time, and then examine each specimen individually at a different selected time interval counted from the initial treatment. When this type of study is carried out using a conventional multiple well dish, the individual studies necessarily involve manipulation of the whole dish containing all 24 specimens. Not only can this be physically inconvenient, but each time a particular specimen is to be studied, all of the specimens must be exposed, which can involve a significant risk of contamination. Also, cross-examination between different cells can occur, for example, due to condensation on the dish cover.

These latter problems can of course be avoided by using a series of individual single cell dishes but then individual dishes are less convenient to manipulate during the initial stages of the study when all of the cells require treatment. There is then also the difficulty of identifying and keeping track of the individual dishes subsequent to the initial treatment step.

An object of the present invention is to provide a specimen tray apparatus which has been specifically designed to address these drawbacks of prior art dishes.

The apparatus provided by the invention is used to hold a plurality of individual specimen vessels, each defining one of said wells and each having an individual, removable cover. The vessels are removably received in an array of openings in a tray which is self-standing on a support surface and which is adapted to co-operate with and simultaneously support all of the vessels when the tray is lifted from said surface.

The apparatus provided by the invention has the advantage that the wells (vessels) can be manipulated individually or collectively depending on the particular operation to be performed. For example, in a kinetic study, all of the wells can be treated similarly and the whole tray placed in a $CO_2$ incubator, and then each individual well (vessel) can be selectively removed from the tray at the appropriate time for individual study. The fact that each well (vessel) has its own individual cover virtually eliminates the possibility of contimation or cross-contimation of other wells when one well is removed for study.

Preferably, the tray has a lid to which the vessel covers can then be removably secured using pressure-sensitive transparent tape so that all or selected ones of the covers can be simultaneously removed with the lid.

In order that the invention may be more clearly understood, reference will now be made to the accompanying drawings which illustrate a preferred embodiment of the invention by way of example, and in which.

Figure 1:
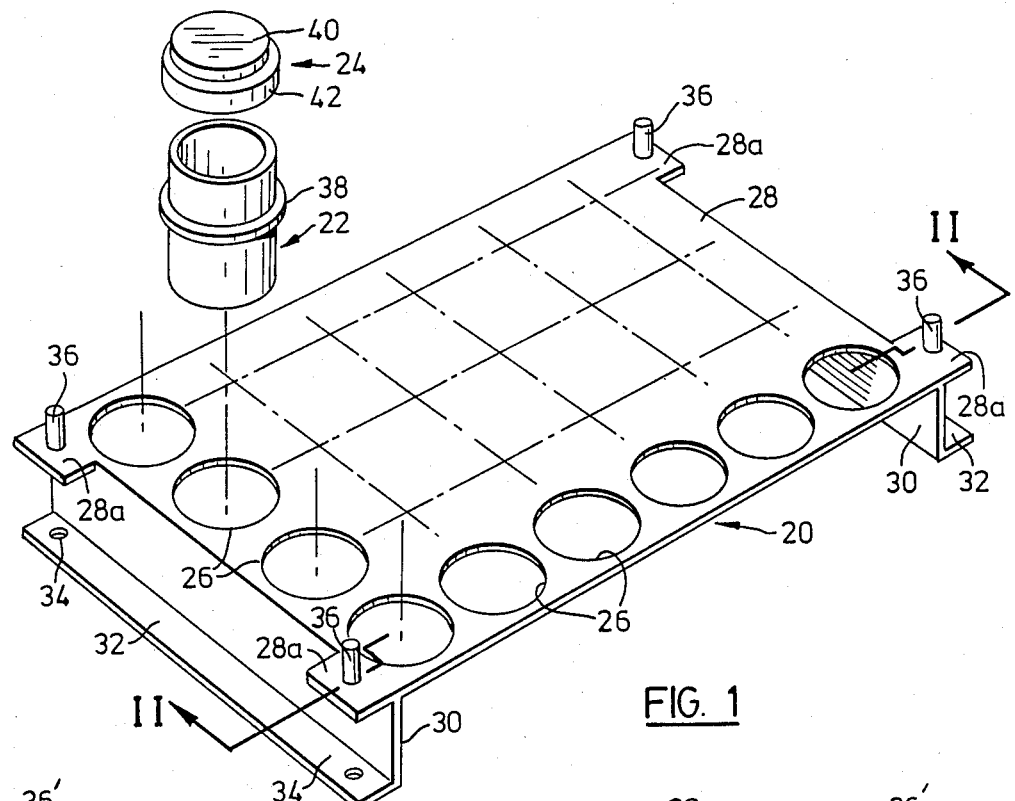
FIG. 1 is a perspective view of the tray of a specimen tray apparatus in accordance with the invention, with one vessel and the associated cover shown in exploded positions above the tray.

Referring first to FIG. 1, the tray of the apparatus is generally indicated by reference numeral 20 and one of a plurality of vessels, each defining a recess or well for receiving a specimen is indicated at 22. The vessel is shown in an exploded position above tray 20 and has a cover 24 which in turn in shown exploded above the vessel. In this particular embodiment, tray 20 is designed to accommodate 24 such vessels arranged in a conventional 6×4 format, and to this end, the tray defines an array of openings into which the vessels can be inserted from above. Some of those openings are shown at 26 in FIG. 1 but, for clarity of illustration, not all 24 have been shown.

Tray 20 includes a horizontal top plate 28 in which the openings 26 are formed and two vertical end walls which depend from opposite ends of plate 28 and which serve to support the plate at a predetermined spacing (see later) above a support surface on which the tray is disposed. Flanges 32 project outwardly from the lower ends of the end walls and are formed with circular openings 34, the purpose of which will become apparent later. Extensions 28a of the top plate extend outwardly beyond the end walls 30 above and parallel to flange 32 at the corners of the top plate. These extensions are formed with cylindrical projections 36 which are dimensioned so as to be complimentary to the openings 34 in flange 32. This arrangement allows several specimen dishes to be stacked in vertically superimposed relationship in the manner shown in FIG. 2, as will be more fully described later.

Before referring to that view, the vessel 22 and its associated cover 24 will be described primarily with reference to FIG. 1. Vessel 22 is of cylindrical shape and has a closed bottom wall. In this particular embodiment, the specimen dish is designed primarily for kinetic cell culture studies and the vessels of the tray are all identical and are dimensioned to provide a liquid capacity of 3.5 ml. and a culture area of 1.9 $cm^2$. The openings 26 in tray 20 are of course circular and are of slightly larger diameter than the external diameter of vessel 22 so that the vessel can easily be inserted downwardly into one of the openings. An external peripheral rib 38 extends around vessel 22 and is of larger diameter than the openings 26 so that the rib will rest on the top surface of plate 28 and permit the plate to support the vessel. In this embodiment, the vessel and tray are designed so that the spacing between the bottom wall of each vessel and the plane on which the tray stands will be 1 mm. This dimension is indicated at D in FIG. 2 and is selected so as to permit microscopic examination of a specimen within vessel 22 using ordinarily available microscopic equipment, without the need to remove the vessel from the tray.

The cover 24 for vessel 22 has a flat top wall 40 and a depending peripheral skirt 42 which is offset outwardly from the perimeter of wall 40 and is designed to fit around the external surface of vessel 22. Cover 24 is in fact designed to be a relatively loose fit on the vessel so that gases can permeate easily.

The top wall 40 of cover 24 is circular in shape and has an external diameter which is substantially equal to the external diameter of vessel 22 away from rib 38. This allows the tray to be fitted with a lid which is physically identical with the tray and which has openings similar to openings 26 for receiving vessel covers as will now be described with reference to FIGS. 2 and 3.

Figure 2:
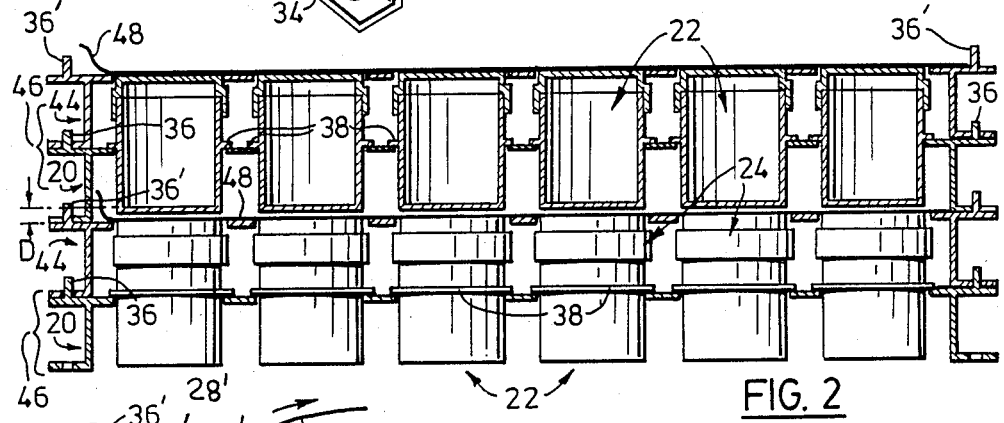
FIG. 2 is a vertical sectional view generally along line II—II of FIG. 1 taken through two specimen tray apparatus of the form provided by the invention, shown stacked one on top of the other; and, FIG. 3 is a view similar to FIG. 2 showing one of the dishes with its lid partly removed.
Figure 3:
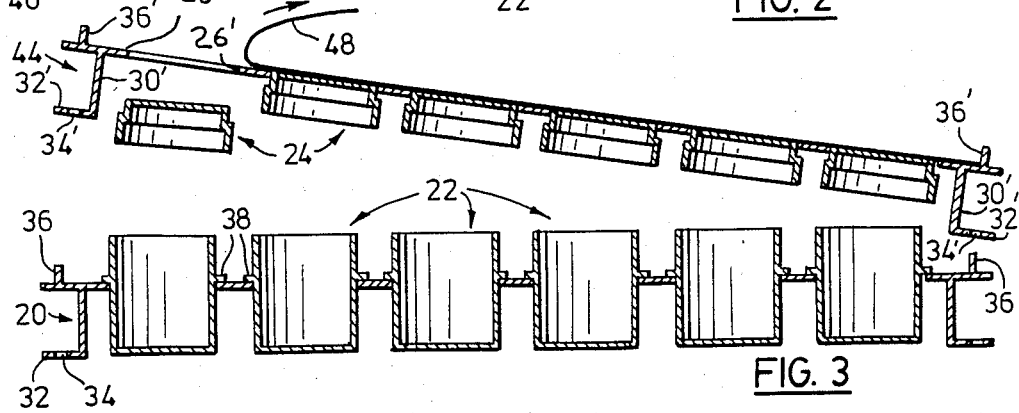

FIG. 3 shows tray 20 in section with a series of vessels 22 in position in the openings in the tray. A lid for the tray is indicated at 44 and is shown partly removed from the tray. Since lid 44 is physically identical with tray 20, parts of the lid which correspond with parts of tray 20 already described in connection with FIG. 1 have been indicated by primed reference numerals in FIGS. 2 and 3. It will be seen from these views that the flanges 32' at the lower ends of the vertical end walls 30' of lid 44 rest on the extensions 28a of the top plate 28 of tray 20 with the projections 36 engaged in the openings 34' of the lid flanges 32'. In this way, the tray and lid are positively located with respect to one another and will not normally be separated other than by deliberately lifting lid 44 generally vertically.

These projections and slots also allow several specimen tray apparatus to be stacked one on top of the other and positively located with respect to one another as best illustrated in FIG. 2. In that view, two apparatus each comprising a tray 20 and a lid 44 are shown stacked one on top of the other. Each apparatus is generally denoted by reference numeral 46 and the two trays and lids are denoted 20 and 44 respectively. It will be seen that the projections 36' of the lid of the lowermost apparatus 46 extend through the openings 34 of the tray of the dish above and thereby positively locate the two apparatus with respect to one another.

A further feature of the apparatus is that the vessels 22 are designed so that, when lid 44 is in place on tray 20, the top walls 40 of the covers 24 will project into the openings 26' in the top plate 28' of the lid 44 and will lie with their top surfaces substantially even with the top surface of the remainder of plate 28', as best shown in FIG. 2. Pressure sensitive tape can then be applied over the top surface of plate 28' and the exposed surfaces of the covers 24 and will releasably secure the covers to the lid. FIG. 3 illustrates the covers being lifted with the lid. That view also shows how the pressure sensitive tape 48 can be peeled back as appropriate to release selected ones of the covers 24.

Depending on the particular purpose for which the apparatus is being used, it would of course be possible to employ a single wide strip of pressure sensitive tape to secure all 24 of the covers to the lid, or to use several narrower strips to secure the covers in rows. This latter arrangement probably would be preferred in that it would allow more convenient release of individual covers or groups of covers as appropriate to the particular technique being performed using the apparatus.

In the case of a kinetic cell culture study, for example, it might be desirable to initially secure all of the covers 24 to the lid 44 so that all of the covers will be lifted from all of the vessels when the lid is removed from the apparatus. Cultures can then be placed in all of the wells and identically treated. When the lid has been replaced, the adhesive tape can then be removed, releasing all of the covers so that each well is effectively sealed from the other wells and can now be manipulated individually. Since the covers will remain in position in the openings in the lid once the lid is replaced, even after the tape has been removed, it will of course be possible to readily replace the tape over one or more of the covers, if required later.

Preferably, clear transparent pressure sensitive tape will be used. The tray, lid, vessels and covers will also preferably be clear and transparent. Each of these components may in fact be moulded in one piece in a suitable transparent and sterilizable plastic material such as polystyrene.

In practice, it may be that a complete assembly comprising a tray, lid and vessels with covers will be sold as a sterile package within a suitable outer wrapper. However, another advantage of the dish provided by the invention is that it is not in fact necessary for the tray and lid to be sterile. Thus, it would also be possible to sell a sterile package containing vessels and covers only, either for use in a customer's own tray and lid or for use with a tray and lid sold separately.

It will of course be understood that the preceding description relates to a particular preferred embodiment of the invention only and that many modifications are possible. For example, the number and configuration of the vessels within the tray may vary. Twenty-four wells has become typical in conventional fixed well dishes and it may be that this will be the most commonly used number of wells. However, in some cases it may be desirable to provide more or less wells, even up to as many as 96. The particular shape of the vessels can of course vary although cylindrical vessels are probably preferred. Also the vessels within any one tray need not all be identical. The particular dimensions given by way of example can also vary of course. Well diameters of 35 or even 50 mm. in diameter may be appropriate in some cases, while in others the diameter may be, say, 15 mm.

I claim:

1. A specimen tray apparatus used to hold a plurality of specimen vessels comprising:
   a tray having an array of openings for receiving specimen vessels, said tray being self-standing on a support surface and being adapted to co-operate with and simultaneously support all of said specimen vessels when the tray is lifted from said support surface;
   a lid adapted to co-operate with said tray and including a top having a top surface and a plurality of openings which are substantially co-incident with said openings in said tray and which openings are adapted to receive covers of said vessels; each of said specimen vessels being removable and having a cover with a generally planar top surface which top surface is accessible through the openings of said lid with said lid in place and said specimen vessels being supported in said tray with said top surfaces of said vessel covers substantially even with the top surface of said lid, so that the covers can be releasably adhered to the lid by pressure-sensitive tape applied across the lid and cover top surfaces.

2. An apparatus as claimed in claim 1, wherein each said tray and lid comprises a plate and depending end walls at respectively opposite ends of said plate, by which the plate can be supported above a surface, said lid end walls being adapted to co-operate with the tray and support the lid thereon.

3. An apparatus as claimed in claim 2, wherein each of said end walls is formed with a laterally directed outwardly extending flange, and wherein said plate includes extensions above said flange, said extensions and flange being formed respectively with locating projections and openings for receiving said projections whereby a tray and lid fitted together are located laterally with respect to one another.

4. An apparatus as claimed in claim 3, wherein said tray and lid are identical to one another, and wherein each said vessel is supported in said tray by a protuberant peripheral rib which rests on an upper surface of said tray plate.

5. An apparatus as claimed in claim 4, wherein each of said vessels is of cylindrical shape and is a one-piece plastic moulding.

6. An apparatus as claimed in claim 1, wherein each of said tray, lid, and each of said vessels and covers is made of a one piece moulding of a sterilizable clear plastic material.

7. An apparatus as claimed in claim 6, wherein said plastic material is clear polystyrene.

8. An apparatus as claimed in claim 1, wherein said array of openings in the tray comprises four rows each containing six circular openings.

* * * * *